United States Patent [19]

Howson et al.

[11] Patent Number: 4,834,152
[45] Date of Patent: May 30, 1989

[54] STORAGE RECEPTACLE SEALING AND TRANSFER APPARATUS

[75] Inventors: David C. Howson, Denver, Colo.; Robert E. Havranek, Danville, Calif.; John A. Popken, Longmont; Frederick L. Stone, Boulder, both of Colo.

[73] Assignee: Intelligent Medicine, Inc., Englewood, Colo.

[21] Appl. No.: 78,409

[22] Filed: Jul. 27, 1987

Related U.S. Application Data

[63] Continuation-in-part of Ser. No. 835,043, Feb. 27, 1986, abandoned, and a continuation-in-part of Ser. No. 833,067, Feb. 26, 1986, Pat. No. 4,722,733.

[51] Int. Cl.$^4$ ............................. B65B 3/02; A61J 1/00
[52] U.S. Cl. ..................................... 141/286; 141/319; 141/329; 141/27; 604/405; 604/411; 604/414; 604/905; 604/415; 604/416
[58] Field of Search ................... 141/21, 28, 320, 319, 141/329, 330, 285, 286; 604/905, 403, 411, 412, 405, 413, 416, 415, 414

[56] References Cited

U.S. PATENT DOCUMENTS

3,005,455 10/1961 Poitras et al. .
3,662,752 5/1972 Yokoyama ..................... 604/411
3,783,895 1/1974 Weichselbaum ................ 604/411
3,938,520 2/1976 Scislowicz et al. ............. 604/405
4,058,121 11/1977 Choksi et al. .
4,201,208 5/1980 Cambio, Jr. .
4,211,588 7/1980 Raines ........................... 604/411
4,253,501 3/1981 Ogle ............................. 141/27
4,259,184 3/1981 D'Arnal ........................ 210/85
4,262,671 4/1981 Kersten ......................... 604/411
4,301,799 11/1981 Pope, Jr. et al. .
4,312,349 1/1982 Cohen .
4,392,850 7/1983 Elias et al. .................... 604/416 X
4,411,661 10/1983 Kersten ......................... 604/411
4,432,760 2/1984 Mittleman et al. ............. 604/405 X
4,573,993 3/1986 Hoag et al. .................... 604/411
4,588,403 5/1986 Weiss et al. ................... 604/411

Primary Examiner—Ernest G. Cusick
Attorney, Agent, or Firm—Robert E. Harris

[57] ABSTRACT

A storage receptacle sealing and transfer apparatus is disclosed for selectively enabling sealing and transfer of material to and from the receptacle. The apparatus is particularly useful for maintaining and later transferring drug and associated materials, under sterile conditions, to achieve mixing, as, is necessary, for example, in reconstituting a drug by mixing the drug with a diluent prior to delivery to a patient. The transfer apparatus is mounted at the aperture, or mouth, of a storage receptacle to seal the aperture until the contents are needed, and then to permit sterile transfer from one receptacle to another receptacle through a central passage. The apparatus also includes venting through one or more passages offset from the central passage for supplying or discharging air into the storage receptacle as needed, and a filter is included in each vent passage, with the filter being permeable to passage of gases, including air, in either direction through the vent passage, but precluding passage of liquid or solid materials or microorganisms in either direction through the vent passage. The central passage and all venting passages are sealed until use, and the central passage also includes a septum in one disclosed embodiment, with a penetrating unit being included for access through the septum to the interior of the storage receptacle for delivery or withdrawal of substance therefrom.

28 Claims, 5 Drawing Sheets

Fig_1

Fig_2

Fig_4

Fig_3

Fig_5

Fig_6

Fig_15

Fig_16

Fig_14

Fig_7

Fig_8

Fig_17

STORAGE RECEPTACLE SEALING AND TRANSFER APPARATUS

RELATED INVENTION

This application is a continuation-in-part of U.S. application Ser. No. 835,043, filed Feb. 27, 1986 and now abandoned, entitled "Material Transfer Apparatus Having Vent With One-Piece Hydrophobic Filter Therein", and U.S. patent application Ser. No. 833,067, filed Feb. 26, 1986 and now U.S. Pat. No. 4,722,733, entitled "Drug Handling Apparatus and Method".

FIELD OF THE INVENTION

This invention relates to a sealing and transfer apparatus, and, more particularly, relates to an apparatus for sealing a storage receptacle having a drug stored therein and transferring material to and from the storage receptacle.

BACKGROUND OF THE INVENTION

It is oftentimes necessary to store a substance and later transfer a material from one receptacle to another and devices for accomplishing this end have heretofore been suggested and/or utilized (see, for example, allowed, copending United States patent application Ser. No. 833,067, commonly assigned to the assignee of this invention, which application is by this reference incorporated herein in its entirety, the issue fee having been paid on June 9, 1987). Such devices have also been heretofore suggested for permitting transfer of drug compoents from a storage receptacle to a delivery receptacle, such as a syringe, and such devices have included vent means to facilitate material transfer when the storage receptacle is retained upright below the vent passage (see, for example, U.S. Pat. Nos. 4,230,112, 4,303,071, and 4,317,448), as well as penetrating units, for example needles and the like, attachable to a syringe for access to the storage receptacle.

Transfer devices have also been heretofore suggested and/or utilized for transferring a diluent from one storage receptacle to a drug retained in a second storage receptacle, and such devices have included an air vent with a filter therein to vent the receptacle positioned below the vent passage (see, for example, U.S. Pat. No. 3,938,520).

While devices have heretofore been suggested and/or utilized for transferring various materials, including transfer of drug components, such devices have not proved to be completely successful in providing a sealing apparatus for a storage receptacle that also includes transfer to and from the receptacle under fully acceptable safe and sterile conditions, allowing the vent passage to be selectively positioned below the receptacle to be vented, preventing formation of a vacuum or back pressure which could hinder material transfer regardless of needed orientation to achieve the desired end and/or cause foreceful release of at least a portion of the contents of the storage receptacle upon access thereto and thus exposure of a user to potentially harmful substances.

SUMMARY OF THE INVENTION

This invention provides an improved apparatus and system for sealing a receptacle and enabling transfer of material to and from the receptacle, and particularly for enabling storing and transferring of drug components from one receptacle to another. The transfer apparatus includes venting through one or a plurality of passages each of which has a filter therein for allowing passage of gases, including air, in either direction, but precluding passage of liquid and solid materials or microorganisms therethrough, with sealing of each passage being provided prior to transfer.

It is therefore an object of this invention to provide an improved apparatus for transferring materials.

It is another object of this invention to provide an improved apparatus for transferring drug components under sterile conditions.

It is still another object of this invention to provide an improved apparatus for transferring drug components that includes venting of the storage receptacle.

It is still another object of this invention to provide an improved apparatus for transferring material that includes venting of the storage receptacle thrugh a filter that allows passage of gases, including air, in either direction through the filter but precludes passage of solid or liquid materials in either direction through the filter.

It is still another object of this invention to provide an improved apparatus for transferring drug components that preserves sterile conditions and yet precludes formation of a vacuum or back pressure that could hinder the effectiveness and/or safety of component transfer.

It is still another object of this invention to provide an improved apparatus for transferring material that is sealed against transfer of gases, microorganisms, liquids and/or solids until a seal exposing the filter to the environment is ruptured.

It is still another object of this invention to provide an improved system for transfer of substance between a receptacle and a delivery device which is initially assembled under sterile conditions and sealed for shipment to a user.

It is yet another object of this invention to provide an improved system for transfer of substance between a receptacle and a delivery device which includes a penetrating unit capable of access through a septum while yet reducing the likelihood of accidental puncturing of the protective wear of a user of the system.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
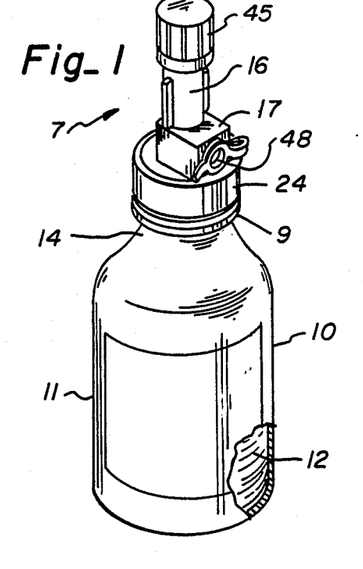
FIG. 1 is a perspective view of the sealing and transfer apparatus of this invention shown mounted on a storage receptacle.

Referring to the drawings, sealing transfer apparatus 7 of this invention is shown mounted at the mouth portion 9 of storage receptacle 10. As shown, receptacle 10 is a vial having a body portion 11, receiving material 12 (such as a diluent or a drug, for example), in the reservoir formed by the body portion, and a neck portion 14 which extends to mouth portion 9 forming an outlet for the storage receptacle.

Apparatus 7 includes upper and lower body portions 16 and 17. Lower body portion 17 has disk 19 mounted thereon, which disk is of a size to span and cover aperture 20 formed by upper annular lip 21 of mouth portion 9 of the vial. Disk 19 preferably has a depending shoulder 22 which snugly fits over the outer wall of lip 21 to mount the apparatus on the storage receptacle. If desired (and as shown), a clamp ring 24 may be provided around the edge of disk 19 and outwardly directed shoulder 25 of the vial to hold the transfer unit against and over the mouth of the vial (alternately welding could be utilized if the vial is formed of plastic material), and a gasket ring 26 may be positioned between lip 21 of the vial and the inner surface of disk 19 to assure establishment of a seal therebetween.

Sealing and transfer apparatus 7 may be formed of any suitable material, such as plastic, for example, and has a central bore, or conduit, 28 therethrough. Bore 28 has an inner port 29, which port opens through disk 19 into the reservoir formed within the storage receptacle, and an outer port 30 at upper body portion 16, with outer port 30 being preferably adapted (as by being provided with tapered walls 31 terminating at opening 33) to receive a like configured portion of delivery receptacle, or unit, 32 (shown in FIG. 4) therein in order to establish communication through bore 28, between the storage receptacle reservoir and the compartment, or reservoir, 34 in delivery receptacle 32.

Figure 3:
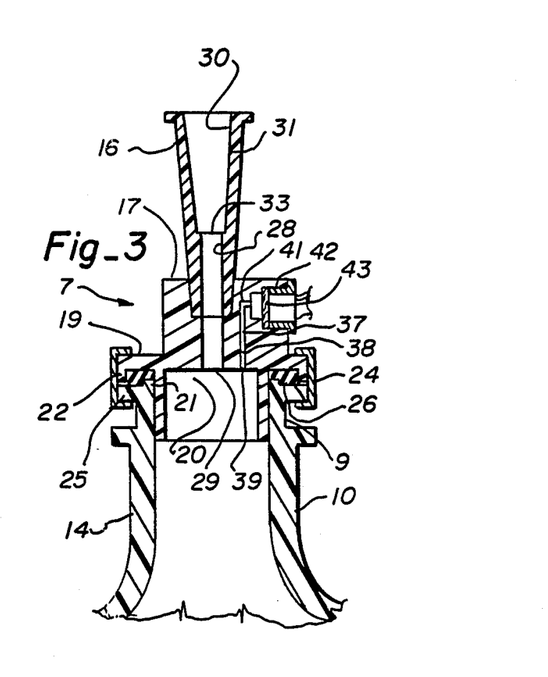
FIG. 3 is an sectional view taken through line 3—3 of FIG. 2.
Figure 4:
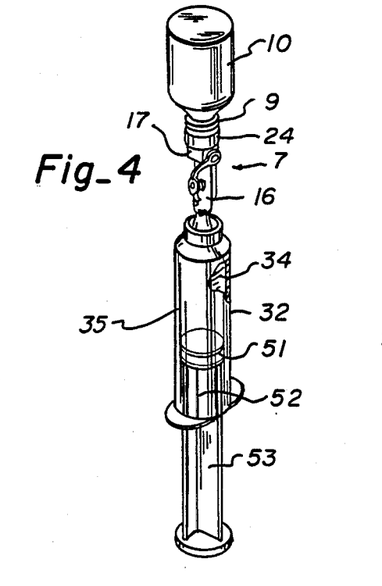
FIG. 4 is a perspective view of the apparatus of this invention shown in position between a storage receptacle and a syringe to transfer material from the storage receptacle to the syringe.

As specifically shown in FIG. 4, delivery receptacle 32 is embodied as a syringe, with compartment 34 being formed by syringe body 35. End, or nozzle, 31 of syringe 32 is preferably tapered, and is snugly received in port 30 of transfer apparatus 7 with the long elastomeric insert of the nozzle forming a seal with the inner walls of port 30 (as indicated in FIG. 3).

Lower, or main, body portion 17 of apparatus 7 has a vent passage, or bore, 37 therein providing a venting conduit, which passage has an inner conduit 38 with port 39 at the inner end thereof, which port opens through disk 19 into the reservoir of the storage receptacle. As shown in FIG. 3, conduit 38 of passage 37 is parallel to but radially offset from central bore 28 so that the ports 29 and 39 are adjacent to, but spaced from, one another. The port openings are preferably flash-free at the ports.

The outer conduit 41 of vent passage 37 extends outwardly from the end of conduit 38 at substantially a right angle so that conduit 41 opens to the side of main body portion 17. As shown in FIG. 3, the outer portion 42 of conduit 41 has an enlarged diameter relative to the remainder of the vent passage, and is of a size to snugly receive filter 43 therein. Filter 43 is a two-way filter that is air permeable (but is impermeable to liquid and solid materials), with the filter preferably being a hdyrophobic (rather than hydrophilic), sterile bacterial filter having, for example, a 0.22 micron port size.

Figure 2:
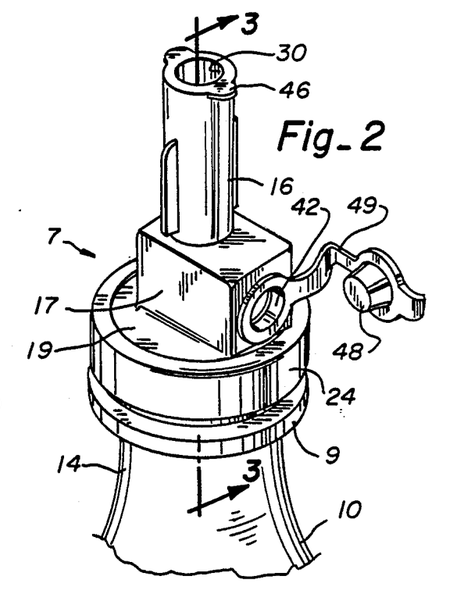
FIG. 2 is an enlarged perspective view primarily illustrating the sealing and transfer apparatus shown in FIG. 1.

Cap 45 (as best shown in FIG. 1) is provided at the end of port 30 at the outer end of central bore 28, and lugs 46 (as best shown in FIG. 2) are provided to releasably lock the cap in position to seal the central bore. In addition, plug 48 is provided for insertion into the vent outer port at the end of enlarged conduit 42 outwardly of filter 43. When in position at the end of the vent passage (as indicated in FIG. 1), a seal is provided thereat. As indicated, plug 48 may have a retainer strap 49 thereon for retaining the strap adjacent to the apparatus when the plug is withdrawn from the position sealing the end of the vent passage (as indicated in FIGS. 2 and 4).

As indicated in FIG. 4, syringe 32 has an actuator, or piston, 51 therein, which piston is moved axially in opposite directions within the syringe body by rod 52, the outer portion 53 of which extends from the rear portion of the syringe for external control purposes.

In operation, the user, using sterile procedures, attaches syringe 32 to vial 10 after moving connector cap 45 from the vial. Vent plug 48 is also removed, and, after inverting the syringe and vial, as shown in FIG. 4, the material (such as diluent, for example), is withdrawn from the vial into the syringe by moving piston 51 rearwardly within syringe 32. Vent 37 allows air to enter vial 10 through filter 43 thus preventing a vacuum from forming and hindering diluent removal. The material in the syringe can then be utilized, as needed, which may be, for example, by mixing with a drug and then delivering the mixture from the syringe to a patient.

Figures 5, 6:
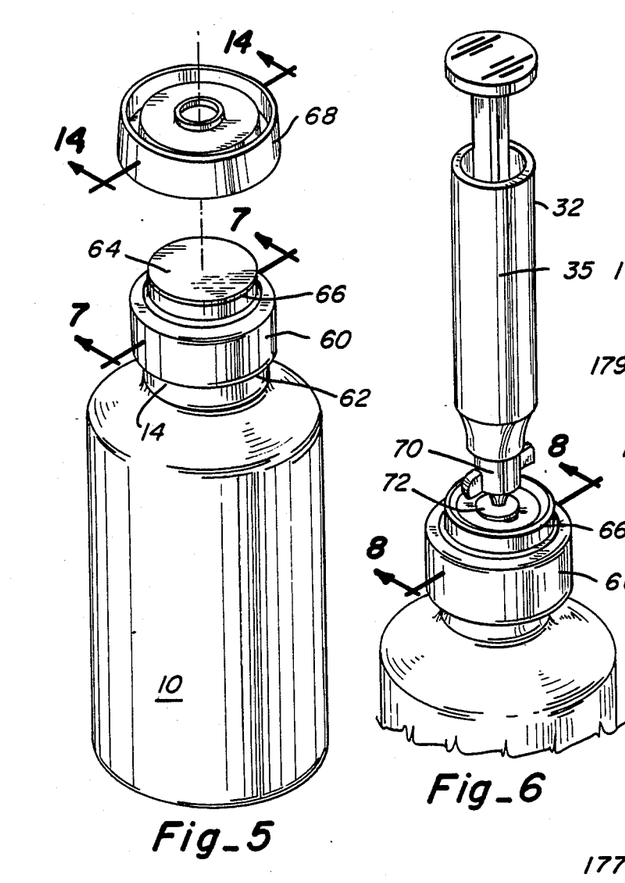
FIG. 5 is a perspective view of the now preferred embodiment of the sealing and transfer apparatus of this invention shown preassembled on a storage receptacle with a protective seal in place thereon and showing the replaceable cap supplied therewith.
FIG. 6 is a perspective view of the embodiment of the apparatus shown in FIG. 5 with the seal removed and with a delivery device positioned to transfer material therethrough.

A second, and now preferred, embodiment of the sealing and transfer apparatus of this invention is shown in FIGS. 5 through 13. Transfer apparatus 60 is shown in FIG. 5 mounted on receptacle 10 at rim 62 of neck 14. Seal 64, a removable disc-shaped seal which may be made of a foil or other suitable material, is positioned and maintained across annular ridge 66 (as by induction heating, adhesive, heat sealing or other conventional means) at the time of assembly of the apparatus 60 on receptacle 10 so that the interior portions of the apparatus and the receptacle may be supplied to a user in a sterile condition. Seal 64 is preferably of a size and configuration to fit closely the size of annular ridge 66, and is preferably made of a layer of aluminum material having a polypropylene layer bonded on each side of the aluminum layer (for example the trade marked product "Safe-gard" produced by 3M Company) so that by heating the aluminum layer when the seal is placed over annular ridge 66 (also preferably made of polypropylene plastic) the polypropylene layer of seal 64 adjacent ridge 66 and the polypropylene of the ridge are melded to provide a substantially complete and reliable seal against contaminants and the like across ridge 66 (and therefore for the filter, septum and contents as more fully set forth hereinbelow). The aluminum also provides a reliable vapor seal. Cap 68 is also preferably provided as more fully set forth hereinbelow.

As shown in FIG. 6, upon removal of the seal 64 from ridge 66 (typically by pulling the seal from its position across annular ridge 66), delivery receptacle, or device 32 having penetrating unit, or nozzle, 70 affixed thereto (penetrating unit 70 being a safety unit which may be provided as part of the overall sealing and transfer system as more fully set forth hereinbelow), is positioned with the penetrating unit 70 inserted through septum 72 of the transfer apparatus 60 for delivery or withdrawal of a substance.

Figure 7:
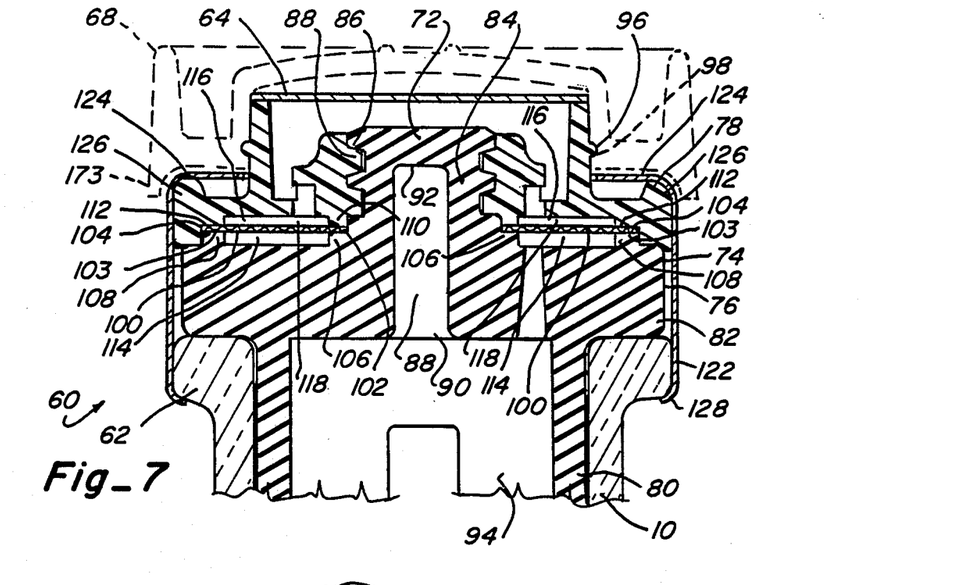
FIG. 7 is a sectional view taken through line 7—7 of FIG. 5.
Figure 8:
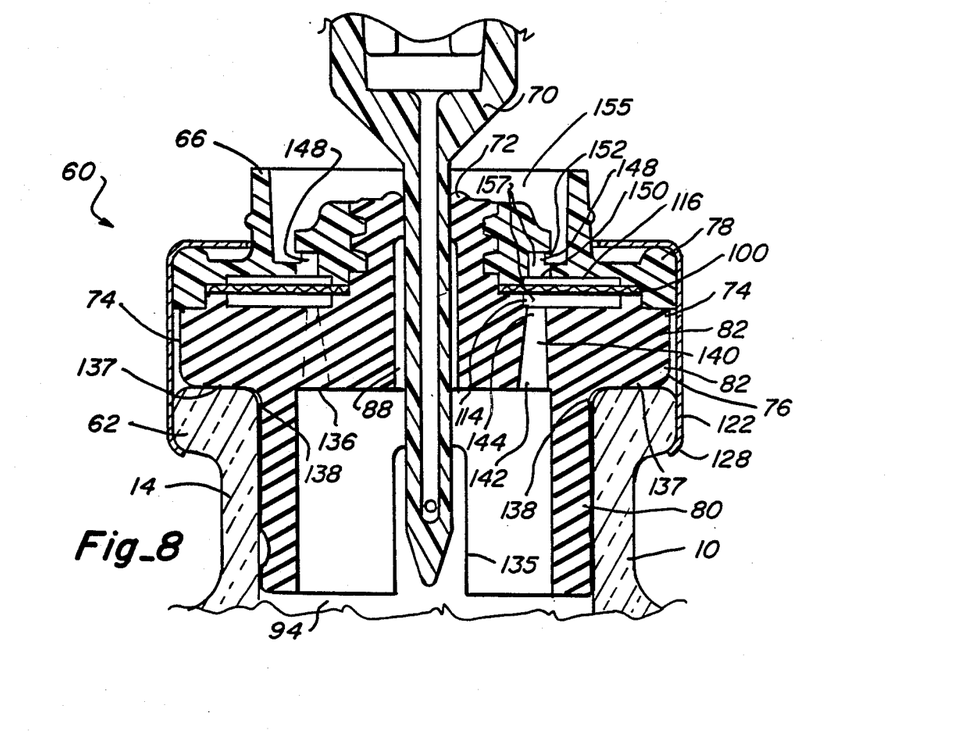
FIG. 8 is a sectional view taken through line 8—8 of FIG. 6.

Turning now to FIGS. 7 and 8, sealing and transfer apparatus 60 is shown to include body 74 including mounting section 76 and upper section 78, with mounting section 76 including lower mounting portion 80, central portion 82 and upper mounting portion 84 including septum 72. Upper section 78 is releasably mounted to mounting section 76 at upper mounting portion 84 at opposed engageable threads 86 and 88 by rotating upper section 78 so that threads 86 and 88 are engaged. Mounting section 76 has bore 88 centrally located in central portion 82. Bore 88 has inner and outer ends 90 and 92, inner end 90 opening to storage reservoir 94 of receptacle 10 and with outer end 92 terminating at septum 72.

Upper section 78 includes annular ridge 66 for maintaining seal 64 thereon, and for maintaining cap 68 when cap 68 is positioned thereover, with cap 68 being maintained thereon at annular protrusion 96 received by annular groove 98 of cap 68.

Filter 100, which is a filter similar in nature to filter 43 described hereinabove, is a circular filter in the form of a thin disc having a central bore 102 for receipt therethrough of upper mounting portion 84 of mounting section 76 (as most advantageously shown in FIGS. 9A and 9B). Filter 100 is maintained between mounting section 76 and upper section 78 at opposed faces 103 and 104 thereof, respectively, being clamped therebetween upon mounting of upper section 78 to upper mounting portion 84 of mounting section 76. Filter 100 is maintained between inner and outer annular ridges 106 and 108 on central portion 82 of mounting section 76 and annular projection 110 and 112 of upper body section 78. An annular chamber 114 is thus provided adjacent one side of filter 100 between ridges 106 and 108. A plurality of chambers 116 are provided adjacent the other side of filter 100, the sections being defined by spines 118 extending radially between projections 110 and 112, spines 118 and projections 110 and 112 normally being in contact with filter 100.

Clamping ring 122 is positioned around apparatus 60, for example by crimping the edges thereof into place, with upper portion 124 thereof being positioned over shoulders 126 of upper section 78 and with lower portion 128 being clamped over lip 62 of receptacle 10 for releasably maintaining transfer apparatus 60 on receptacle 10 (clamping ring 122 being removable by straightening of the lower portion 128). Ring 122 can be constructed of metal, plastic, or any other suitably rigid material, and is typically positioned while applying pressure to compress sections of the apparatus between upper portion 124 and lower portion 128 of ring 122.

As best shown in FIG. 8, lower mounting section 76 is maintained in receptacle 10 by lower mounting portion 80, an annular wall extending away from central portion 82 and receivable through throat 14 of receptacle 10. Mounting portion 80 has slits 135 (only one of which is shown in FIG. 8) for allowing compressibility of the mounting portion 80 when pressed into place in outlet opening 136 of receptacle 10 at throat 14 to assure a tight fit within throat 14. Lower wall 137 of central portion 82 and upper wall section 138 of lower mounting portion 80 form a seal with rim 62 of receptacle 10 for maintaining a sterile environment within reservoir 94 when ring 122 is positioned around apparatus 60.

Figure 10:
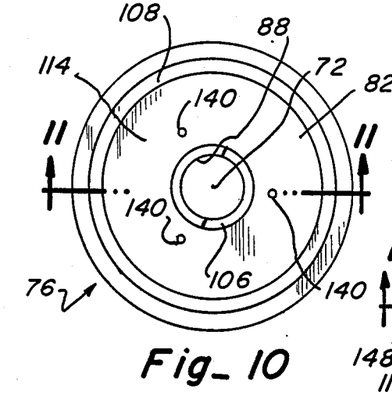
FIG. 10 is a top view of the mounting section shown in FIG. 9A.

A plurality of venting conduits 140 pass through central portion 82 of mounting section 76 spaced equidistant from central bore 88 (as shown in FIG. 10) with inner ports 142 communicating with reservoir 94 and an outer ports 144 communicating with chamber 114 below filter 100. Conduits 140 are small by comparison to bore 88, inner ports 142 preferably having a diameter of 0.035 inches and outer ports 144 preferably having a diameter of 0.020 inches compared to the preferable diameter of bore 88 of 0.09 inches (it being understood that the particular dimensions and numbers of ports may vary as dictated by design and/or application). A plurality of venting conduits 148 (as best viewed in FIG. 12) pass through upper section 78 of body 74 (only two of which can be seen in FIG. 8) having inner ports 150 each communicating with a different chamber 116 above filter 100 and outer ports 152 in communication with the exterior of receptacle 10 as well as apparatus 60 at open area 155. Each of the venting conduits 140 and 148, filter 100 and chambers 114 and 116 thus provide an overall path, or conduit, 157 through body 74 of apparatus 60 for venting and filtering of gases therethrough (with filter 100 limiting passage of liquid and/or solid material therethrough as set forth hereinabove) upon removal of substance from, or transfer of substance to, reservoir 94 of receptacle 10 through penetrating unit 70 when inserted through septum 72.

Figure 9A:
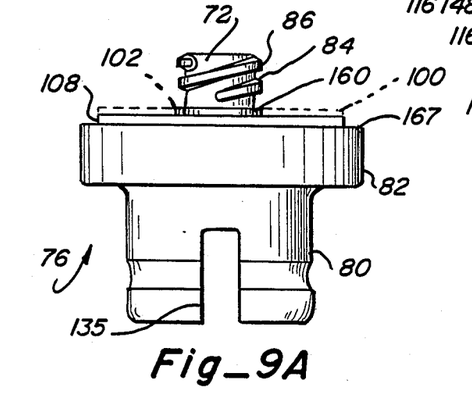
FIG. 9A is a side view of the mounting section of the apparatus shown in FIGS. 7 and 8.
Figure 9B:
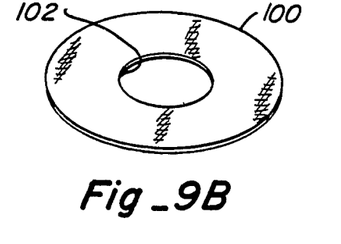
FIG. 9B is a perspective view of the filter used in the sealing and transfer apparatus as shown in FIGS. 7, 8 and 9A.
Figures 11, 13:
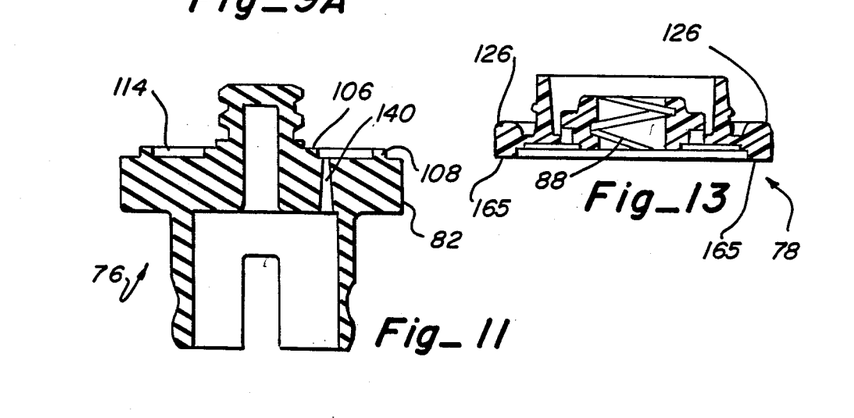
FIG. 11 is a side sectional view taken through lines 11—11 of FIG. 10.
FIG. 13 is a side sectional view taken through lines 13—13 of FIG. 12.

Mounting section 76 of body 74 is shown in FIGS. 9A, 10 and 11. Upper mounting portion 84 is shown to include threads 86 for maintaining upper section 78 thereon. Annular ring 160 is provided to assure a snug fit of central bore 102 of thin, disc-shaped filter 100 (shown in FIG. 9B) over mounting portion 84.

As shown in FIGS. 10, three conduits 140 are shown through central portion 82 of mounting section 76. Venting conduits 140 thus communicate between the interior of the receptacle and the chamber 114 provided between annular ridges 106 and 108 at central portion 82.

Figure 12:
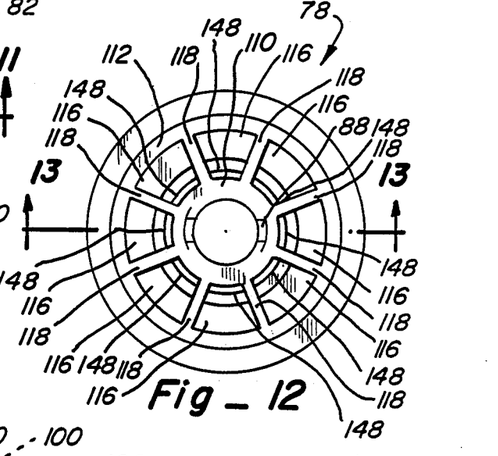
FIG. 12 is a bottom view of the upper section of the apparatus shown in FIGS. 7 and 8.

FIGS. 12 and 13 show upper section 78 of body 74. As shown in FIG. 12, inner and outer projections 110 and 112 and radially extending spines 118 provide a contact surface for filter 100 and thereby define chambers 116 adjacent to the. Venting conduits 148 communicate with the chambers 116, each to a different chamber. Central bore 162 having mating threads 88 defined in the wall thereof is provided for mounting of the upper section to the mounting section of body 74 by rotating one section to thereby clamp filter 100 in place and to seal the two sections.

As shown in FIG. 13, annular lip 165 is provided around the outer circumference of upper section 78, at shoulder 126 for providing a sealing relationship with outer annular surface 167 of central portion 82 of mounting section 76 (as shown in FIG. 9) when the sections are rotated to operational position. Chamber 114 of lower mounting section 76 is thus separated by the filter from chambers 116 of upper section 78 of the body 74 of transfer apparatus 60, providing a plurality of discreet venting conduits between the interior of receptacle 10 and the exterior of the receptacle and sealing and transfer apparatus 60.

Figure 14:
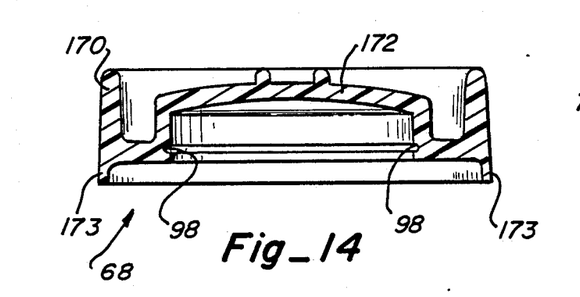
FIG. 14 is a side sectional view of the replaceable cap taken through line 14—14 of FIG. 5.

FIG. 14 shows cap 68 including annular grip 170 at the outer portions thereof and inner cap section 172 for covering septum 72 and outer ports 152 of conduits 148. Annular wall 173 is provided to snugly fit over shoulder 126 of upper section 78 (as shown in FIG. 7). Annular groove 98 for receipt of annular protuberance 96 (as shown in FIG. 7) is provided at the interior of central cap portion 172. The cap is provided for resealing between uses of the apparatus 60, to thereby maintain a more sterile condition between uses and after removal of seal 64.

Figure 15:
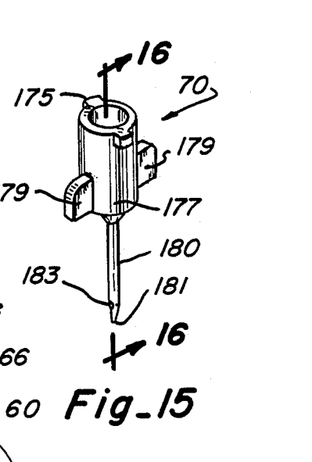
FIG. 15 is a perspective view of the safety pentrating unit shown mounted on a syringe in FIGS. 6 and 8.
Figure 16:
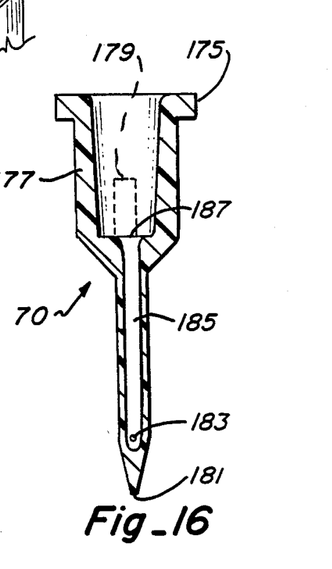
FIG. 16 is a side sectional view taken through line 16—16 of FIG. 15.

FIGS. 15 and 16 show the penetrating unit 70 preferably utilized in the overall system including sealing and transfer apparatus 60, cap 68, seal 64 and penetrating unit 70. Thue unit includes luer lock 175 for receipt of the unit at an opening in body portion 35 of syringe 32, a body portion 177 including gripping means 179 for use when applying the unit 70 to the syringe, and a penetrating portion 180 having a blunt end 181 and inlets 183 offset from blunt end 181 and exiting outwardly from the side of penetrating portion 180, two such outlets being preferably provided.

As shown in FIG. 16, inlets 183 communicate with conduit 185, with the conduit 185 having an opening 187 into body 179 and thus to body portion 35 of syringe 32.

Penetrating unit 70 (preferably made of plastic or the like), by providing blunt end 181, which is capable of penetrating septum 72 (as shown in FIG. 6), provides greater safety for a user, the blunt end 181 being less likely to pierce or rend safety apparel of the user, and thus decreases the likelihood of exposure to potentially dangerous substances.

Figure 17:
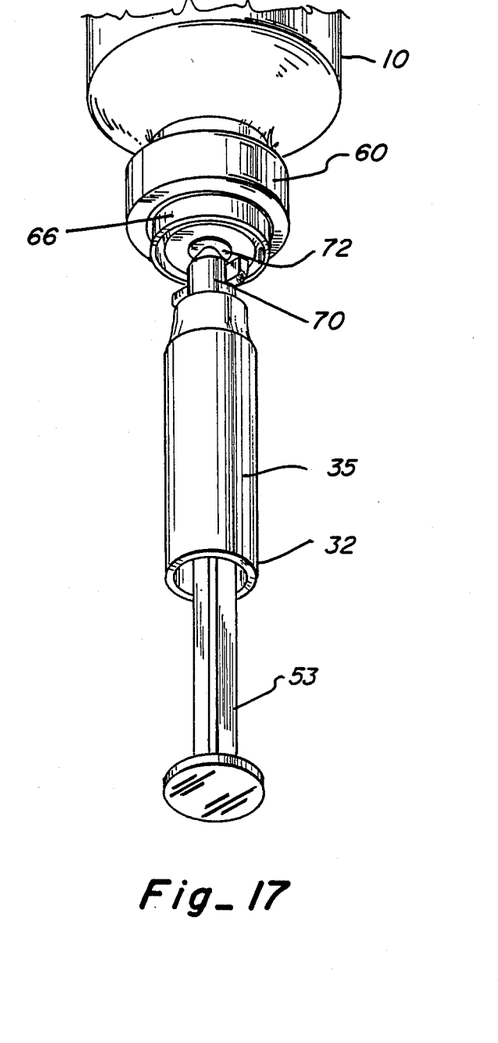
FIG. 17 is a perspective view of the sealing and transfer apparatus as shown in FIG. 6 illustrating use of the apparatus while in an inverted position for withdrawal of substance from a storage receptacle.

In operation, as best illustrated in FIGS. 5, 6, 8, and 17, when the apparatus is received by a user, seal 64 must be initially removed before first use, thereby exposing septum 72 and outer ports 152 of conduits 148. Between uses (and typically before first use) a user will cleanse both the penetrating unit 70 and septum 72, whereupon unit 70 is inserted through the septum for transfer of substance to receptacle 10, as shown in FIG. 6 with receptacle 10 typically upright and thus having conduit 157 above reservoir 94, or withdrawal of substance from the receptacle, as shown in FIG. 17 with receptacle 10 typically positioned above conduit 157.

As shown in FIG. 8, when substance is being transferred to the receptacle, venting of gases for prevention of a build-up of positive or negative relative pressure within reservoir 94 is provided for through overall venting path, or conduit, 157 through filter 100, with filter 100 accommodating the flow of gas through the conduit while preventing passage therethrough of liquid and/or solid materials or microorganisms when, for example, the reservoir is positioned above the conduit as illustrated in FIG. 17. After withdrawal of penetrating unit 70 from septum 72, replaceable cap 68 may be placed over the septum and conduits to provide a cover therefore.

As shown in FIGS. 8 and 17 the storage receptacle 10 may be located either above or below the delivery receptacle 32. It is also to be understood that material transfer may be accomplished with the storage receptacle in any position intermediate between above and below the delivery receptacle. Because there are no moving parts in the transfer system, and because the parts making up the transfer system are compactly and firmly held in relative position to each other, the material transfer process may be effectively and safely carried out even when the apparatus is subject to mechanical shocks or vibration during the transfer process.

Mounting section 76 of apparatus 60 is advantageously constructed of a rubber compound or the like, and upper section 78 and cap 68 may be constructed plastic materials, such as polypropylene, for example. While a syringe has been utilized to illustrate operation of apparatus 60, it is to be appreciated that apparatus 60, as well as penetrating unit 70, could be utilized in other combinations, such as gravity transfer systems and the like.

As can be appreciated from the foregoing, this invention provides an improved sealing and transfer apparatus and system for sealing a receptacle and for transferring material, particularly drug and associated drug materials, between receptacles.

What is claimed is:

1. A sealing and transfer apparatus for selectively sealing a substance within a storage reservoir of a storage receptacle and transferring the stored substance from the storage reservoir through an outlet opening from said reservoir, said apparatus comprising:

a body portion having a central bore therein, said central bore having inner and outer ends, at least said outer end having a septum positioned thereacross adapted to engage a portion of a unit having an opening therein for receiving said substance when transferred from said storage receptacle;

mounting means at one part of said body portion for enabling said transfer apparatus to be sealably mounted at said outlet opening of said storage receptacle; and a venting conduit extending through said body portion and having first and second chambers therein, said first chamber being defined by inner and outer annular ridges, said venting conduit also having an inner port communicating with said storage reservoir when the transfer apparatus is mounted on said storage receptacle at said oulet opening thereof, and an outer port opening externally of said transfer apparatus, said venting conduit having a one-piece micropore hydrophobic filter therein between said first and second chambers so that one part of each of said ridges is in contact with said filter, said filter allowing passage of gas therethrough in either direction but precluding passage of liquid or solid materials therethrough in either direction independent of the relative positions of said storage receptacle and said venting conduit and with said venting conduit thereby requiring no check valve positioned therein.

2. The apparatus of claim 1 wherein said apparatus includes a cap removably mountable over said septum and over said outer port of said venting conduit to seal said septum and said venting conduit.

3. The apparatus of claim 1 wherein said apparatus further comprises a plurality of venting conduits extending through said body portion and having inner ports communicating with said storage reservoir when said transfer apparatus is mounted on said storage receptacle at said outlet opening thereof, and outer ports opening externally of said transfer apparatus.

4. The apparatus of claim 3 wherein said filter in said plurality of venting conduits is a single filter positionable to provide filtering for all said plurality of conduits.

5. The apparatus of claim 1 wherein said apparatus is initially assembled on said storage receptacle in a sterile environment, and wherein said apparatus further comprises a removable seal mounted over said septum and said outer port of said venting conduit to maintain said sterile condition until first use by a user of said apparatus.

6. The apparatus of claim 1 wherein said body portion includes a first section having said mounting means thereat and a second section, wherein said central bore extends through said first section, and wherein said venting conduit extends through said first and said second sections, said one-piece micropore hydrophobic filter being maintained between said first and said second sections.

7. A sealing and transfer apparatus for selectively sealing a substance within a storage reservoir of a storage receptacle and transferring the stored substance from the storage reservoir through an outlet opening into said reservoir, said apparatus comprising:
a body portion;
mounting means at one part of said body portion adapting said transfer apparatus to be releasably mounted at said outlet opening of storage receptacle;
a first conduit extending through said body portion and having first and second spaced ports with said first port communicating with said storage reservoir through said outlet opening in said storage receptacle when said transfer apparatus is mounted on said storage receptacle at said outlet thereof, and with said second port being adapted to engage a portion of a unit having an opening therein for receiving said substance when transferred from said storage receptacle;
a filter for allowing passage of gas through said filter in either direction but precluding passage of liquid or solid materials therethrough in either direction; and
venting conduit means spaced from said first conduit having first and second chambers positioned on opposite sides of said filter, said first chamber being defined by inner and outer annular ridges, one part of each of said ridges being in contact with said filter, and with said filter forming one wall of each of said chambers, said venting conduit means having a plurality of first passages extending between said first chamber and said storage reservoir, and a plurality of second passages extending from said second chamber to a position external of said storage reservoir.

8. The apparatus of claim 7 wherein said first conduit includes a septum.

9. The apparatus of claim 7 wherein said first and second chambers of said venting conduit means are annular chambers having inner and outer annular chamber walls, said inner chamber walls being adjacent said first conduit.

10. The apparatus of claim 10 wherein said filter is a thin, disc-shaped, one-piece hydrophobic filter having a central bore therethrough for mounting thereof around said first conduit.

11. The apparatus of claim 2 wherein said second chamber is defined by inner and outer annular projections, said annular projections each having one part adjacent to said filter, and wherein said filter is maintained between said projections and said ridges.

12. The apparatus of claim 11 further comprising a plurality of radially extending spines positioned between said inner and outer projections defining said second chamber so that said second chamber is divided into a plurality of chambers, each said plurality of second passages extending from a different one of said plurality of second chambers.

13. The apparatus of claim 7 wherein said plurality of first passages each have a smaller cross sectional area than the cross sectional area of said first conduit.

14. The apparatus of claim 13 wherein said plurality of first passages each have first and second ports, said first port opening to said storage reservoir, and said second port opening to said first chamber, and wherein said first port has a greater cross sectional area than said second port.

15. The apparatus of claim 7 wherein said plurality of first and second passages each are smaller in cross sectional area than said first conduit.

16. A sealing and transfer apparatus for selectively sealing a substance within a storage reservoir of a storage receptacle and transferring the stored substance between a storage reservoir through an outlet opening into said reservoir and a delivery unit having an opening therein for receiving said substance, said apparatus comprising:
a body portion having a first section sealably mountable at said outlet opening of said storage receptacle and a second section releasably mountable on said first section;
a first conduit extending through said body portion and having first and second spaced ports with said first port communicating with said storage reservoir through said outlet opening in said storage receptacle when said body portion is mounted on said storage receptacle at said outlet thereof, and with said second port communicating externally of said storage receptacle and said body portion; and
at least one first venting conduit extending through said body portion and having an inner port communicating with said storage reservoir when said body portion is mounted on said storage receptacle at said outlet opening thereof, and an outer port opening externally of said storage receptacle and said body portion, said at least one first venting conduit having a filter thereat for allowing passage of gas through said at least one first venting conduit in either direction, but precluding passage of liquid or solid materials therethrough.

17. The apparatus of claim 16 wherein said first section includes an upper mounting portion for mounting of said second section thereon outwardly of said first conduit, said upper mounting portion including a septum therein.

18. The apparatus of claim 17 further comprising a penetrating means for penetrating said septum for transfer of said substance between said storage receptacle and said delivery unit, said penetrating means including a penetrating portion having a blunt closed end capable of penetrating said septum.

19. The apparatus of claim 17 wherein said apparatus further comprises a plurality of venting conduits and wherein said filter is a disc-shaped, one-piece hydrophobic micropore filter having a central bore therethrough for mounting thereof on said upper mounting portion.

20. The apparatus of claim 16 wherein said first and second sections of said body portion include adjacent faces when said second section is mounted on said first section, said filter being maintained between said adjacent faces, and wherein said face of said first section includes inner and outer annular ridges for defining a first chamber at one side of said filter, and wherein said face of said second section includes inner and outer annular projections for defining a second chamber at the other side of said filter, said face of said second section having a plurality of spines radially extending between said inner and outer annular projections of said face of said second section for dividing said chamber thereat thereby providing a plurality of chambers adjacent to said filter.

21. The apparatus of claim 16 wherein said apparatus further comprises a seal positioned on said second section of said body portion and covering said first conduit and said at least one first venting conduit, said seal being removable upon first use of the apparatus by a user.

22. The apparatus of claim 21 wherein at least a portion of said second section of said body portion adjacent said seal and at least a portion of said seal adjacent said second section of said body portion are made of polypropylene, said seal also having a heat conductive portion, and wherein said seal is removably joined ot said second section by induction heating to provide a substantially complete and reliable seal against contaminants for said first conduit, said at least one first venting conduit and said filter after production of said apparatus and before first use thereof.

23. The apparatus of claim 16 wherein said apparatus further comprises a removable cap positionable on said body portion for covering said first conduit and said at least one first venting conduit between uses of the apparatus.

24. A sealing and transfer system for selectively sealing a substance within a storage receptacle at a storage reservoir and transferring the substance between the storage receptacle and a delivery unit, said storage receptacle having a rim defining an outlet opening into said reservoir, and said delivery unit having an opening therein for receiving said substance, said system comprising:
a first body section having a lower mounting portion, a central portion and an upper mounting portion, said lower mounting portion adapting said first body section to be mountable at said outlet opening of said storage receptacle so that a seal is established at said rim thereof, said upper mounting portion including a septum therein, and said central portion including inner and outer annular ridges;
a second body section adapted to be mountable on said upper mounting portion of said first body section;
a central bore in said first body section having inner and outer ends, said inner end opening to said storage reservoir when a said first body section is mounted at said outlet opening of said storage receptacle, and said outer end terminating at said septum in said upper mounting portion of said first body section;
at least a first venting conduit extending through said first body section and having an inner port communicating with said storage reservoir when said first body section is mounted at said outlet opening of said storage receptacle and an outer port opening externally of said storage receptacle;
at least a first venting conduit extending through said second body section and having an inner port communicating with said outer port of said at least first venting conduit through said first body section and an outer port opening externally of said storage receptacle and said first and second body sections;
a filter mountable on said inner and outer annular ridges of said central portion of said first body section thereby providing a chamber between said filter and said central portion of said first body section and adapted to be maintained between said first and second body sections and between said outer port of said at least first venting conduit through said first body section and said inner port of said at least first venting conduit through said second body section with said outer port of said at least first venting conduit through said first body section opening into said chamber, said filter for allowing passage of gas therethrough in either direction, but precluding passage of liquid or solid materials therethrough; and
a disposable, removable seal at said second body section and adapted to cover and seal said septum of said first body section and said outer port of said at least first venting conduit extending through said second body section for maintaining said septum and said outer port of said at least first venting conduit in a sterile condition until removal of said seal for first use of said system by a user.

25. The system of claim 24 wherein said system further comprises a penetrating unit adapted to be mounted at said opening of said delivery unit after removal of said seal, and having a first portion adapted to be received through said septum of said upper mounting portion of said first body section and a conduit having at least first and second ports, said first port communicating with said storage reservoir when said first body section is mounted at said outlet opening of said storage receptacle and said first portion is received through said septum, and said second port communicating with said opening of said delivery unit when said penetrating unit is mounted thereat.

26. The system of claim 24 wherein said second body section includes a face adjacent said annular ridges of said first body section when said second body section is mounted thereon, said face having inner and outer annular projections opposite said annular ridges of said central portion of said first body section and a plurality of spines extending radially between said inner and outer annular projections of said face of said second body section, said spines and said inner and outer annular ridges of said face of said second body section thereby providing a plurality of chambers at an opposite side of said filter from said chamber between said filter and said central portion of said first body section, said inner port of said at least first venting conduit extending through said second body section communicating with said plurality of chambers.

27. The system of claim 24 wherein said upper mounting portion of said first body section comprises a threaded appendage, said septum residing within said threaded appendage, and wherein said second body section includes a central threaded bore, said central threaded bore and said threaded appendage being matable.

28. The system of claim 24 wherein said system further comprises a removable cap mountable on said second body section and covering said septum in said upper mounting portion of said first body section and said outer port of said at least first venting conduit extending through said second body section between uses of the system by a user.

* * * * *